(12) United States Patent
Andrews et al.

(10) Patent No.: US 7,279,678 B2
(45) Date of Patent: Oct. 9, 2007

(54) METHOD AND APPARATUS FOR COMPOSITION ANALYSIS IN A LOGGING ENVIRONMENT

(75) Inventors: A. Ballard Andrews, Wilton, CT (US); Jacques Jundt, Bethel, CT (US); Robert J. Schroeder, Newtown, CT (US); Bhavani Raghuraman, Wilton, CT (US); Oliver C. Mullins, Ridgefield, CT (US)

(73) Assignee: Schlumber Technology Corporation, Ridgefield, CT (US)

( * ) Notice: Subject to any disclaimer, the term of this patent is extended or adjusted under 35 U.S.C. 154(b) by 109 days.

(21) Appl. No.: 11/203,743

(22) Filed: Aug. 15, 2005

(65) Prior Publication Data

US 2007/0035737 A1    Feb. 15, 2007

(51) Int. Cl.
*G01V 8/00* (2006.01)
(52) U.S. Cl. .................................. 250/269.1
(58) Field of Classification Search ............. 250/269.1
See application file for complete search history.

(56) References Cited

U.S. PATENT DOCUMENTS

| | | |
|---|---|---|
| 3,780,575 A | 12/1973 | Urbanosky |
| 3,859,851 A | 1/1975 | Urbanosky |
| 4,286,327 A | 8/1981 | Rosenthal et al. |
| 4,860,581 A | 8/1989 | Zimmerman et al. |
| 4,994,671 A | 2/1991 | Safinya et al. |
| 5,029,245 A | 7/1991 | Keranen et al. |
| 5,167,149 A | 12/1992 | Mullins et al. |
| 5,201,220 A | 4/1993 | Mullins et al. |
| 5,257,086 A | 10/1993 | Fateley et al. |
| 5,266,800 A | 11/1993 | Mullins |
| 5,331,156 A | 7/1994 | Hines et al. |
| 5,859,430 A | 1/1999 | Mullins et al. |
| 5,929,245 A | 7/1999 | Grund et al. |
| 5,939,717 A | 8/1999 | Mullins |
| 6,075,595 A | 6/2000 | Malinen |
| 6,401,529 B1 * | 6/2002 | Robison et al. .......... 73/152.19 |
| 6,465,775 B2 | 10/2002 | Mullins et al. |

(Continued)

FOREIGN PATENT DOCUMENTS

GB         2402476 A         8/2004

(Continued)

OTHER PUBLICATIONS

Keranen et al., "Semiconductor emitter based 32-channel spectrophotometer module for real-time process measurements", SPIE vol. 1266 In-Process Optical Measurements and Industrial Methods (1990), pp. 91-98.

(Continued)

*Primary Examiner*—Constantine Hannaher
(74) *Attorney, Agent, or Firm*—David Delos Larson; Vincent P. Loccisano; Jody Lynn DeStefanis

(57) ABSTRACT

Methods and apparatus for analyzing a hydrocarbon mixture are disclosed, comprising at least one light-emitting diode (LED) and at least one photodetector positioned to detect energy transmitted by the LED through a sample of the hydrocarbon mixture. In at least one embodiment an optical filter is coupled to the output of the LED to mitigate the adverse effects of the LED's sensitivity to temperature.

34 Claims, 11 Drawing Sheets

U.S. PATENT DOCUMENTS

| | | | |
|---|---|---|---|
| 6,476,384 | B1 | 11/2002 | Mullins et al. |
| 6,995,360 | B2 | 2/2006 | Jones et al. |
| 7,095,012 | B2 | 8/2006 | Fujisawa et al. |
| 2004/0069942 | A1* | 4/2004 | Fujisawa et al. ......... 250/269.1 |
| 2005/0007583 | A1 | 1/2005 | DiFoggio |

FOREIGN PATENT DOCUMENTS

| | | |
|---|---|---|
| WO | 81/00775 A1 | 3/1981 |
| WO | 98/03842 A1 | 1/1998 |
| WO | 01/23848 A1 | 4/2001 |
| WO | 02/066964 A2 | 8/2002 |

OTHER PUBLICATIONS

Malinen et al., "Thirty-two Channel LED array Spectrometer module with compact optomechanical construction", SPIE vol. 1533 Optomechanics and Dimensional Stability (1991), pp. 122-128.

Malinen et al., "Nondispersive and Multichannel analyzers based on mid-IR LEDs and arrays", SPIE vol. 2069. pp. 95-101.

Malinen et al., "LED-based NIR spectrometer module for hand-held and process analyser applications", Sensors and Actuators B 51 (1998). pp. 220-226.

Malinen et al., "LED-based Spectrometer Modules for Hand-Held Sensors and On-Line Process Monitoring", SPIE Proceedings vol. 3537, Nov. 1998.

Panish et al., "Temperature Dependence of the Energy Gap in GaAs and GaP", Journal of Applied Physics, vol. 40, No. 1, Jan. 1969. pp. 163-167.

Y. P. Varshni, "Temperature Dependence of the Energy Gap in Semiconductors", Physica 34, 1967, pp. 149-154.

Betancourt et al., "Analyzing Hydrocarbons in the Borehole", Oilfield Review, Autumn 2003, pp. 54-61.

Dong et al., "In-Situ Contamination Monitoring and GOR Measurement of Formation Fluid Samples", SPE 77899, 2002.

Dong et al., "Downhole Measurement of Methane Content and GOR in Formation Fluid Samples", SPE 81481, 2003.

Dong et al., "Advances in Downhole Contamination Monitoring and GOR Measurement of Formation Fluid Samples", SPWLA 2003.

* cited by examiner

METHOD AND APPARATUS FOR COMPOSITION ANALYSIS IN A LOGGING ENVIRONMENT

FIELD OF THE INVENTION

The present invention relates generally to downhole fluid analysis applicable to formation evaluation and testing in the exploration and development of hydrocarbon-producing wells, such as oil or gas wells. More particularly, the invention provides methods and apparatus for performing downhole analysis on fluids produced in such wells using light-emitting diodes (LEDs).

BACKGROUND OF THE INVENTION

In order to evaluate the nature of underground formations surrounding a borehole, it is often desirable to obtain and analyze samples of formation fluids from various specific locations in the borehole. Over the years, various tools and procedures have been developed to enable this formation fluid evaluation process. Examples of such tools can be found in U.S. Pat. No. 6,476,384 ("the '384 patent"), the entirety of which is hereby incorporated by reference.

As described in the '384 patent, Schlumberger's repeat formation tester (RFT) and modular formation dynamics tester (MDT) tools are specific examples of sampling tools. In particular, the MDT tool includes a fluid analysis module for analyzing fluids sampled by the tool. FIG. 9 illustrates a schematic diagram of such a downhole tool 10 for testing earth formations and analyzing the composition of fluids from the formation. Downhole tool 10 is suspended in a borehole 12 from a logging cable 15 that is connected in a conventional fashion to a surface system 18. Surface system 18 incorporates appropriate electronics and processing systems for control of downhole tool 10 and analysis of signals received from downhole tool 10.

Downhole tool 10 includes an elongated body 19, which encloses a downhole portion of a tool control system 16. Elongated body 19 also carries a selectively-extendible fluid admitting/withdrawal assembly 20 (shown and described, for example, in U.S. Pat. No. 3,780,575, U.S. Pat. No. 3,859,851, and U.S. Pat. No. 4,860,581, each of which is incorporated herein by reference) and a selectively-extendible anchoring member 21. Fluid admitting/withdrawal assembly 20 and anchoring member 21 are respectively arranged on opposite sides of elongated body 19. Fluid admitting/withdrawal assembly 20 is equipped for selectively sealing off or isolating portions of the wall of borehole 12, such that pressure or fluid communication with the adjacent earth formation is established. A fluid analysis module 25 is also included within elongated body 19, through which the obtained fluid flows. The obtained fluid may then be expelled through a port (not shown) back into borehole 12, or sent to one or more sample chambers 22, 23 for recovery at the surface. Control of fluid admitting/withdrawal assembly 20, fluid analysis module 25, and the flow path to sample chambers 22, 23 is maintained by electrical control systems 16, 18.

An optical fluid analyzer (OFA), which may be located in fluid analysis module 25, may identify the fluids in the flow stream and quantify the oil and water content. U.S. Pat. No. 4,994,671 (incorporated herein by reference) describes an exemplary OFA that includes a testing chamber, a light source, a spectral detector, a database, and a processor. Fluids drawn from the formation into the testing chamber by fluid admitting/withdrawal assembly 20 are analyzed by directing light at the fluids, detecting the spectrum of the transmitted and/or backscattered light, and processing the information (based on information in the database relating to different spectra), in order to characterize the formation fluids.

U.S. Pat. No. 5,167,149 and U.S. Pat. No. 5,201,220 (both of which are incorporated by reference herein) also describe apparatuses for estimating the quantity of gas present in a fluid stream. A prism is attached to a window in the fluid stream and light is directed through the prism to the window. Light reflected from a window/fluid flow interface at certain specific angles is detected and analyzed to indicate the presence of gas in the fluid flow.

As set forth in U.S. Pat. No. 5,266,800 (incorporated herein by reference), monitoring optical absorption spectrum of fluid samples obtained over time may allow one to determine when formation fluids, rather than mud filtrates, are flowing into the fluid analysis module 25. Further, as described in U.S. Pat. No. 5,331,156, by taking optical density (OD) measurements of the fluid stream at certain predetermined energies, oil and water fractions of a two-phase fluid stream may be quantified.

In each of the foregoing examples, broad-spectrum incandescent lamps, such as tungsten-halogen lamps, are conventionally used as the light sources for transmitting light through the fluid sample. Although broad-spectrum incandescent light sources provide relatively bright light throughout the near-infrared wavelength spectra, the amount of energy required to power such incandescent light sources can exceed the available power budget.

In addition, because broad-spectrum incandescent light sources cannot be digitally modulated, mechanical optical chopper wheels (with accompanying chopper motors) are conventionally provided to mitigate the effects of 1/f noise. Optical choppers wheels and their respective motors are, however, relatively bulky, expensive and subject to mechanical failure. Moreover, because broad-spectrum incandescent light sources fail to satisfy the stringent vibrational, shock, temperature and size demands of the measurement-while-drilling (MWD), logging-while-drilling (LWD) and production-logging (PL) tool environments, such incandescent light sources have conventionally only been adapted for use in the wireline tool environment.

Accordingly, there exists a need for an apparatus and method capable of analyzing formation fluids in a downhole environment under reduced power constraints. In addition, there is a need for apparatus and methods capable of withstanding the rigors of the MWD, LWD and PL tool environments. There is also a need for apparatus and methods having a light source that is capable of digital modulation, thereby obviating the need for optical mechanical chopper wheels and motors. Preferably, such an apparatus and method would provide significant improvements in efficiency, size and reliability.

SUMMARY OF THE INVENTION

The present invention provides a number of embodiments directed towards improving, or at least reducing, the effects of one or more of the above-identified problems. According to at least one embodiment, an apparatus for analyzing a hydrocarbon mixture comprises at least one light-emitting diode (LED) and at least one photodetector positioned to detect energy transmitted by the LED through a sample of the hydrocarbon mixture or back scattered from the hydrocarbon mixture. This apparatus may further comprise at least one optical bandpass filter for filtering the energy transmitted by the LED. The parameters of the optical bandpass filter may be chosen to mitigate a temperature dependent wavelength shift of the LED and/or to allow passage of a pre-selected wavelength band. According to some embodiments, this pre-selected wavelength band corresponds to at least one spectral characteristic of hydrocarbon. In addition, the bandwidth of the optical bandpass filter may be between 15-20 nm.

In certain embodiments, the photodetector is an Indium Gallium Arsenide (InGaAs) photodiode. The parameters of the LED and the optical bandpass filter may also be selected to enable analysis of live hydrocarbon mixtures in a downhole environment.

In some embodiments, a plurality of LEDs are arranged in a matrix and a plurality of photodetectors are arranged in a matrix and respectively positioned to detect energy transmitted by the plurality of LEDs through the sample. A plurality of optical bandpass filters may also be provided for respectively filtering the energy transmitted by the plurality of LEDs. In addition, a response curve of each of the plurality of photodetectors may be respectively matched to parameters of the plurality of optical bandpass filters.

According to certain embodiments, the apparatus further comprises a processor for controlling the operation of the plurality of LEDs, for digitally modulating the plurality of LEDs, and for analyzing the sample. The apparatus may also further comprise a transimpedance amplifier, an input of which is connected to an output of the plurality of photodetectors, a lock-in amplifier, an input of which is connected to an output of the transimpedance amplifier, and an analog-to-digital converter, an input of which is connected to an output of the lock-in amplifier and an output of which is connected to the processor.

In at least one embodiment, the apparatus further comprises a cooling element, such as a Peltier element, in thermal connection with the plurality of LEDs. The apparatus may also comprise focusing optics positioned between the plurality of optical bandpass filters and the sample for focusing the energy transmitted by the plurality of LEDs. In certain embodiments, the focusing optics focus the energy transmitted by the plurality of LEDs into a collimated beam.

In at least one embodiment, a subterranean sample analysis tool is provided comprising a plurality of light-emitting diodes (LEDs) arranged in a matrix, and a plurality of photodetectors arranged in a matrix and respectively positioned to detect energy transmitted by the plurality of LEDs through a live hydrocarbon mixture. This subterranean sample analysis tool may further comprise a plurality of optical bandpass filters for respectively filtering the energy transmitted by the plurality of LEDs.

In certain embodiments, a method for analyzing a hydrocarbon mixture comprises transmitting energy through a sample of the hydrocarbon mixture using at least one light-emitting diode (LED), and detecting the energy transmitted through the sample using at least one photodetector. The method may include inserting a downhole sampling tool into a borehole and drawing down the sample of the hydrocarbon mixture. The method may further comprise filtering the energy transmitted by the LED using at least one optical bandpass filter. Parameters of the optical bandpass filter may be chosen to mitigate a temperature dependent wavelength shift of the LED and/or to allow passage of a pre-selected wavelength band corresponding to at least one spectral characteristic of hydrocarbon. According to some embodiments, the parameters of the LED and the optical bandpass filter are selected so as to enable analysis of live hydrocarbon mixtures in a downhole environment.

According to at least one embodiment of the method, a plurality of LEDs are arranged in a matrix, and a plurality of photodetectors are arranged in a matrix and respectively positioned to detect energy transmitted by the plurality of LEDs through the sample. The method may further comprise respectively filtering the energy transmitted by the plurality of LEDs using a plurality of optical bandpass filters. In addition, the method may further comprise respectively matching a response curve of each of the plurality of photodetectors to parameters of the plurality of optical bandpass filters.

In certain embodiments, the method further comprises controlling the operation of the plurality of LEDs using a processor, digitally modulating the plurality of LEDs using the processor, and analyzing spectral characteristics of the sample using the processor. The method may also comprise cooling the plurality of LEDs using a cooling element and/or focusing the energy transmitted by the plurality of LEDs into the sample using focusing optics.

Another aspect of the invention provides a method comprising characterizing a live downhole fluid sample using a downhole LED. Using a downhole LED may comprise transmitting LED energy to the sample downhole, detecting the LED energy transmitted from the sample downhole, and communicating detected LED energy measurements uphole to surface electronics.

These and other embodiments and features will be more fully understood upon reading the following detailed description in conjunction with the accompanying drawings and claims.

BRIEF DESCRIPTION OF THE DRAWINGS

The accompanying drawings illustrate embodiments of the present invention and are a part of the specification. Together with the following description, the drawings demonstrate and explain the principles of the present invention.

Figure 1:
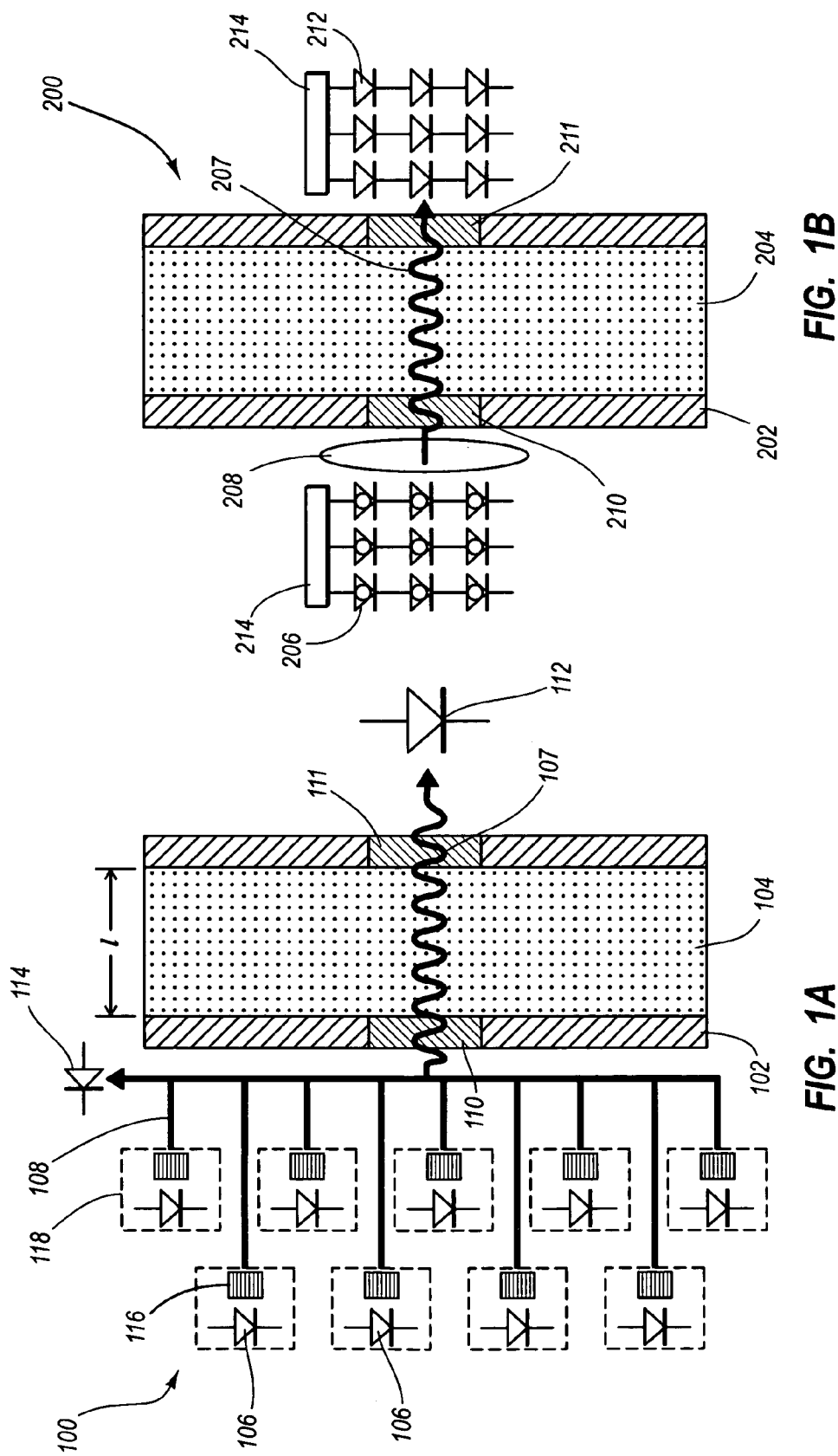
FIG. 1A and FIG. 1B illustrate schematic diagrams of exemplary fluid analysis cells for analyzing extracted samples of formation fluids according to embodiments of the present invention.

Throughout the drawings, identical reference characters and descriptions indicate similar, but not necessarily identical elements. While the present invention is susceptible to various modifications and alternative forms, specific embodiments have been shown by way of example in the drawings and will be described in detail herein. However, one of skill in the art will understand that the present invention is not intended to be limited to the particular forms disclosed. Rather, the invention covers all modifications, equivalents and alternatives falling within the scope of the invention as defined by the appended claims.

DETAILED DESCRIPTION OF EXEMPLARY EMBODIMENTS

Illustrative embodiments and aspects are described below. One of ordinary skill in the art will appreciate that in the development of any such embodiment, numerous implementation-specific decisions must be made to achieve the developers' specific goals, such as compliance with system-related and business-related constraints, which will vary from one implementation to another. Although such a development effort might be complex and time-consuming, the same would nevertheless be a routine undertaking for those of ordinary skill in the art having the benefit of this disclosure.

As used throughout the specification and claims, the terms "borehole" or "downhole" refer to a subterranean environment, particularly in a borehole. The words "including" and "having," as used in the specification and claims, have the same meaning as the word "comprising."

Figure 9:
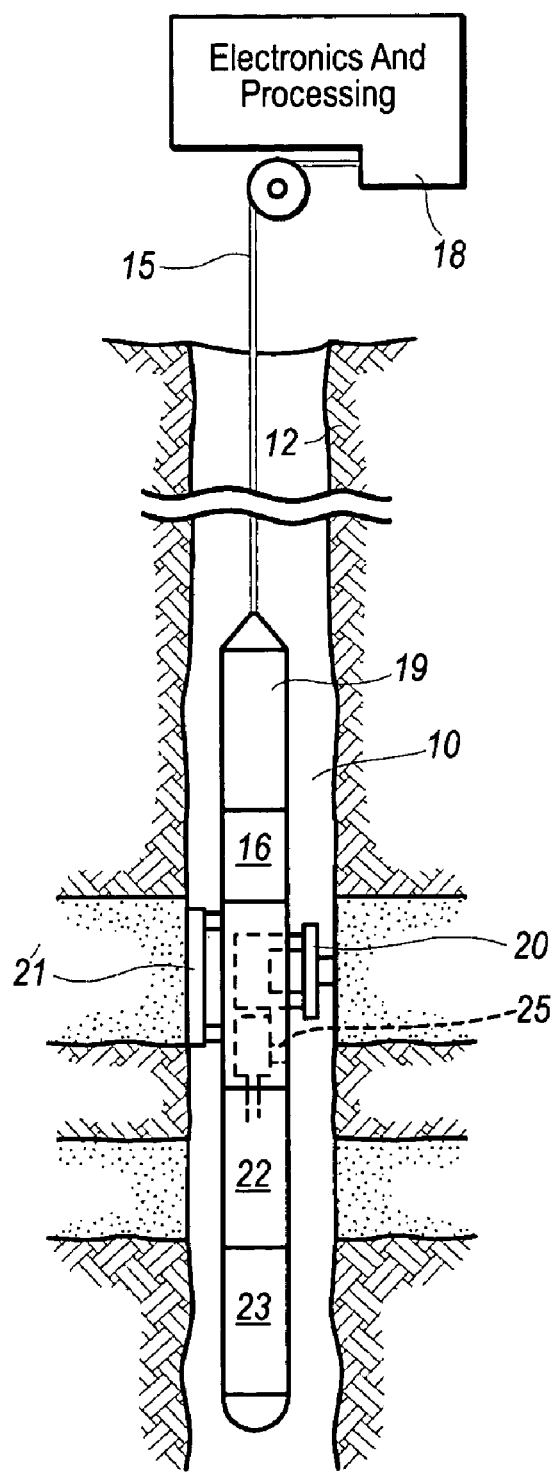
FIG. 9 illustrates an exemplary downhole tool in which a fluid analysis cell according to principles of the present invention may be implemented.

FIG. 1A illustrates a schematic diagram of an exemplary fluid analysis cell 100 for analyzing extracted samples of formation fluids. Exemplary fluid analysis cell 100 may be adapted for use in a number of environments and/or included in a number of different tools. For example, fluid analysis cell 100 may form a portion of a fluid analysis module 25 housed in a downhole tool 10, as illustrated in FIG. 9.

According to at least one embodiment, exemplary fluid analysis cell 100 comprises a flowline 102 housing an extracted formation fluid sample 104. Formation fluid sample 104 may be extracted, withdrawn, or admitted into flowline 102 in any number of ways known to those of skill in the art. For example, as detailed in U.S. Pat. No. 3,780,575 and U.S. Pat. No. 3,859,851 (both of which are hereby incorporated by reference), sample 104 may be admitted into flowline 102 by a fluid admitting/withdrawal assembly 20, illustrated in FIG. 9. As detailed above, fluid admitting/withdrawal assembly 20 (FIG. 9) admits fluid samples by selectively sealing off or isolating portions of the wall of borehole 12 (FIG. 9).

Exemplary fluid analysis cell 100 also comprises at least one LED 106 acting as a light source. In certain embodiments, LED 106 may be optically coupled via optical cabling 108 to a sample window 110 formed in flowline 102. Optical cabling 108 represents any form of optical cabling known in the art, including, for example, fiber optic cable. In addition, sample window 110 may be formed of any generally transparent material capable of transmitting light, including, for example, sapphire, glass and so on.

In addition to being optically coupled to sample window 110, LED 106 may also be optically coupled via optical cabling 108 to a reference photodetector 114. Reference photodetector 114 may be formed generally of any suitable semiconducting material capable of detecting photon light emissions. For example, reference photodetector 114 may be an Indium-Gallium-Arsenide (InGaAs) photodiode or a Silicon (Si) photodiode.

When LED 106 is forward-biased by a power source (described more fully in connection with FIG. 8 below), spontaneous photon emission (electro-luminescence) occurs as electron-hole pairs recombine. In at least one embodiment, these photons of light 107 spontaneously emitted by LED 106 are directed by optical cabling 108 onto sample window 110. The photons of light 107 are then transmitted through sample window 110, across fluid sample 104, and through a second sample window 111. The light 107 that passes through the second sample window 111 is then detected by photodetector 112. As with reference photodetector 114, photodetector 112 may be formed generally of any suitable semiconducting material capable of detecting photon light emissions. For example, photodetector 112 may be an Indium-Gallium-Arsenide (InGaAs) photodiode or a Silicon (Si) photodiode.

In at least one embodiment, the fractional composition of a formation fluid may be determined by using exemplary fluid sample cell 100 to examine the light absorbed by a sample of the formation fluid, such as formation fluid sample 104. Specifically, Beer's law states that the fraction of light absorbed per unit path length in a sample depends on the composition of the sample and the wavelength of the transmitted light. This relationship can be expressed as:

$$OD = A = -\log_{10}T = -\log_{10}\left(\frac{I_0}{I}\right), \tag{1}$$

where OD is the optical density of the fluid sample, A is the absorbance at a specific wavelength, T is the transmittance of the fluid sample, $I_0$ is the intensity of the light incident upon the sample, and I is the intensity of the light after passing through the sample (transmitted light intensity).

Thus, in accordance with Eq. 1, the absorbance or optical density of a formation fluid may be determined by measuring the ratio of incident light $I_0$ to transmitted light I through an optical cell containing an extracted sample of the formation fluid having a specified path length l. Returning to FIG. 1A, the intensity of incident light $I_0$ emitted by LED 106 is measured by reference photodetector 114, while the intensity of the light I transmitted through sample 104 is measured by photodetector 112. By arranging for the light emitted by LED 106 to reach reference photodetector 114 directly without passing through fluid sample 104, drift in the power source and/or other processing electronics may be compensated for. Since the path length l is known, the optical density of fluid sample 104 may be computed in accordance with Eq. 1 once the intensities of lights $I_0$ and I have been measured. In many embodiments, path length l is equal to approximately 2 mm.

Figure 2:
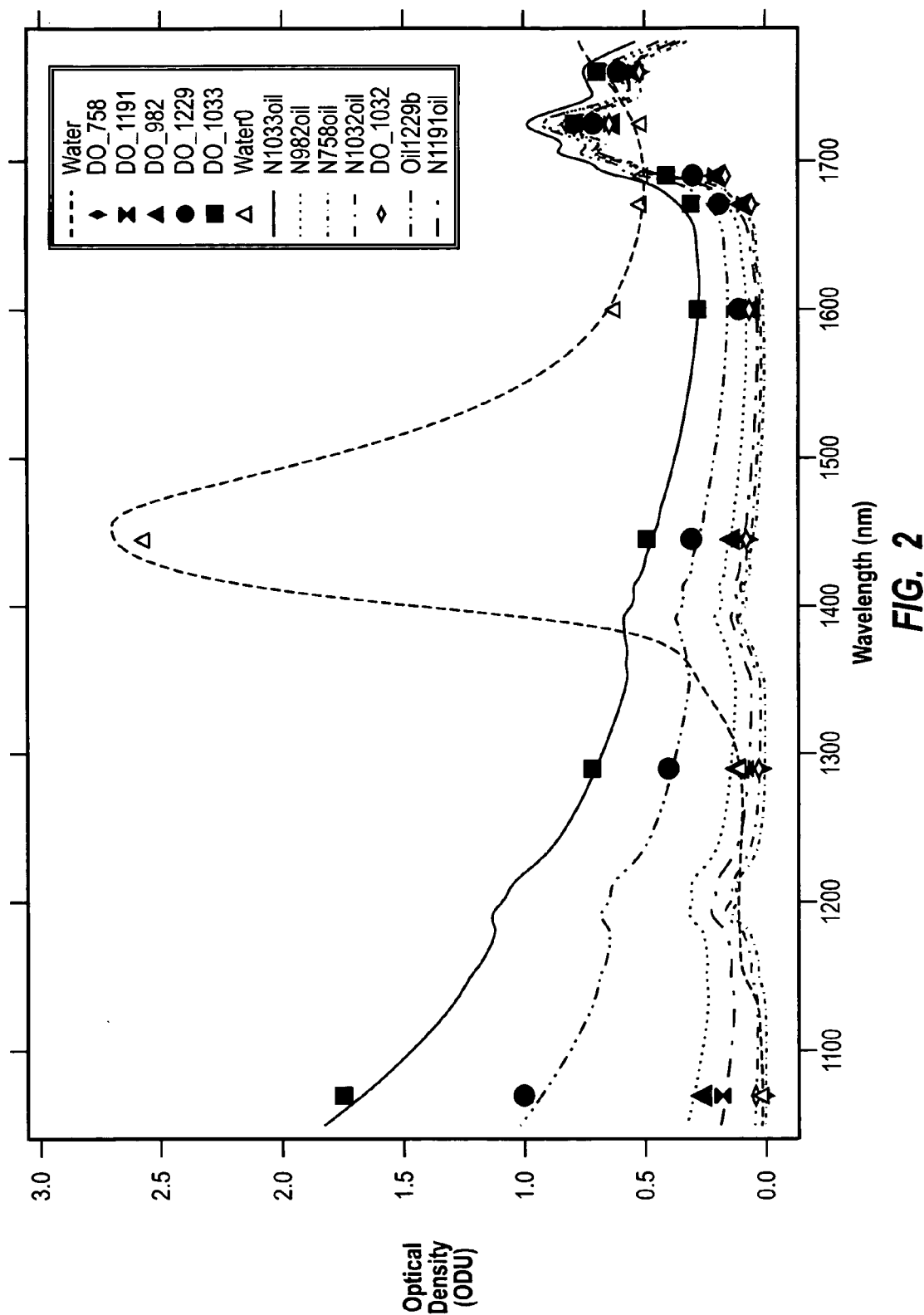
FIG. 2 is a chart illustrating the optical density of a variety of fluids.

FIG. 2 is a chart illustrating the optical density or absorbance of a variety of fluids measured using a commercial spectrometer. The lines (solid, dashed, dotted, etc.) in FIG. 2 represent measurements taken in a series of continuous scans using a commercial grating spectrometer, while the shapes (circles, squares, diamonds, etc.) represent discrete points measured using a filter spectrometer. As seen in this figure, water absorbs strongly at 1445 nm, methane absorbs strongly at 1671 nm and oil absorbs strongly at 1725 nm. The vibrational bands of hydrocarbon mixtures are also shown as being located between 1600 nm and 1780 nm.

Thus, since the absorption wavelengths of various formation fluids are generally known or are readily ascertainable using commercial spectrometers, Beer's law enables a user of exemplary fluid analysis cell 100 to ascertain the presence and amount of various known chemical compositions in fluid sample 104. For example, if a user were interested in ascertaining whether and in what amount carbon-dioxide ($CO_2$) was present in a fluid sample 104, the user need only choose an LED 106 having a wavelength equal to the wavelength of carbon-dioxide's peak absorption wavelength (2008 nm). The amount of carbon-dioxide present in fluid sample 104 may then be computed in accordance with Eq. 1 once the intensities of incident and transmitted lights $I_0$ and I are measured.

With respect to the composition and selection of LED 106 in exemplary fluid analysis cell 100, since the vibrational bands of hydrocarbon are located between 1600 nm and 1780 nm, LED 106 may be formed of III-V chemical compounds to ensure radiation in the visible and near-infrared spectra. As will be known to those of skill in the art having the benefit of this disclosure, the wavelength of light emitted by a LED depends upon the bandgap energy of the materials used to form the LED's p-n junction. In addition, the junction temperature of an LED, and hence the wavelength and intensity of light emitted by the LED, are known to be sensitive to both the LED's ambient operating temperature and the magnitude of its driving current. The LED's sensitivity to temperature proves especially problematic in downhole environments, where temperatures can meet and even exceed 165° C.

Thus, when adapting fluid analysis cell 100 for use in downhole environments, the spectral characteristics and output power of each LED 106 must be measured as a function of temperature to ensure each is capable of satisfying the temperature demands of downhole environments. In at least one embodiment, the spectral characteristics of each LED 106 may be observed with a grating or filter monochromer as ambient temperature is increased. The optical power of each LED 106 may also be simultaneously monitored as temperature is increased.

Expressed mathematically, maximum emission intensity occurs at:

$$\lambda_p \cong \frac{1.24}{E_{gap}}, \quad (2)$$

where $\lambda_p$ is the peak wavelength and $E_{gap}$ is the bandgap energy. The full width at half maximum (FWHM) of the LED emission spectra is:

$$FWHM = 1.45 * \lambda_p^2 * k_B T, \quad (3)$$

where $k_B$ is Boltzmann's constant (approximately $1.3807 \times 10^{-23}$ J/K) and T is the absolute temperature (in Kelvin).

Figure 3A:
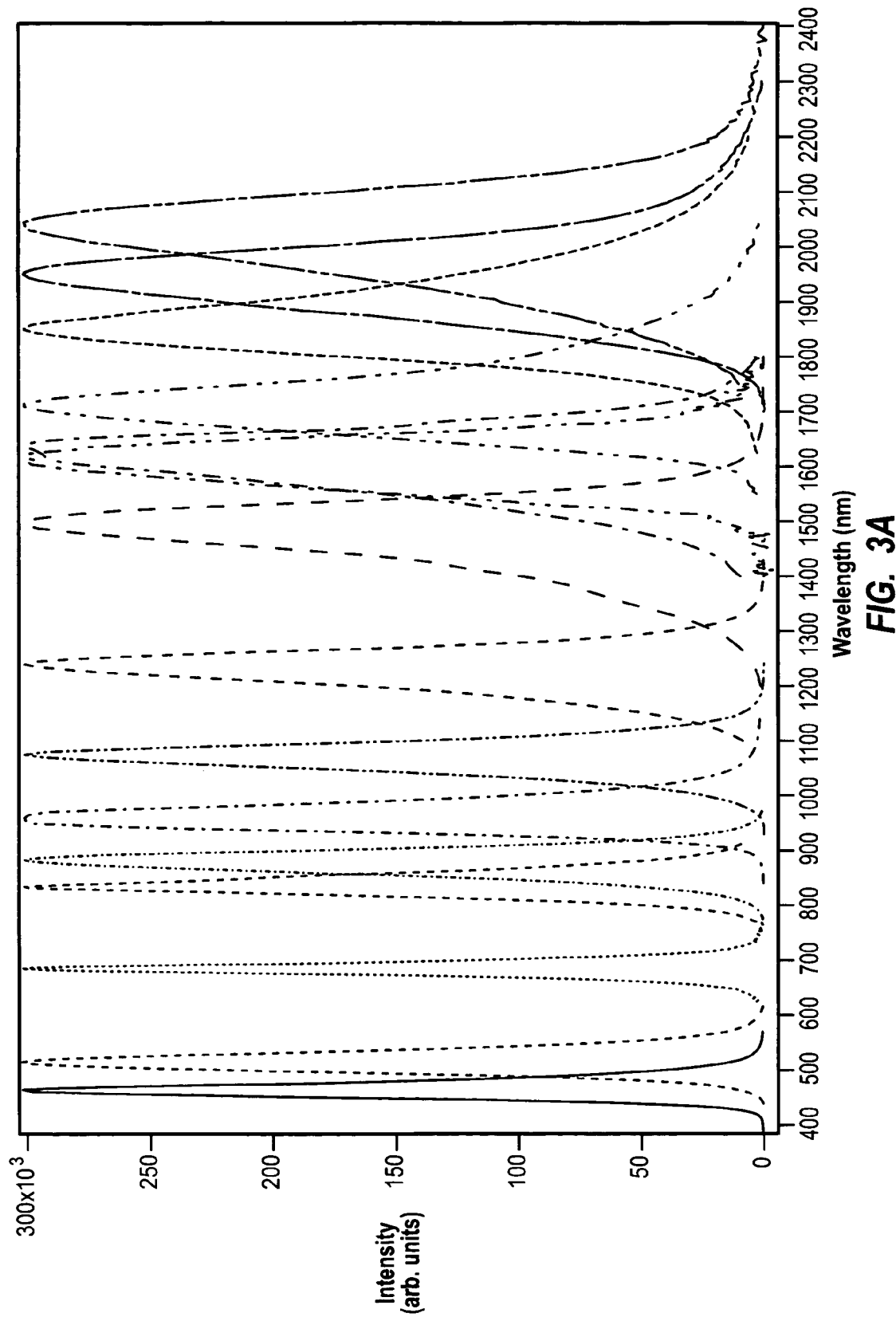
FIG. 3A is a chart illustrating the spectra of a variety of LEDs formed of III-V semiconductor compounds.
Figure 3B:
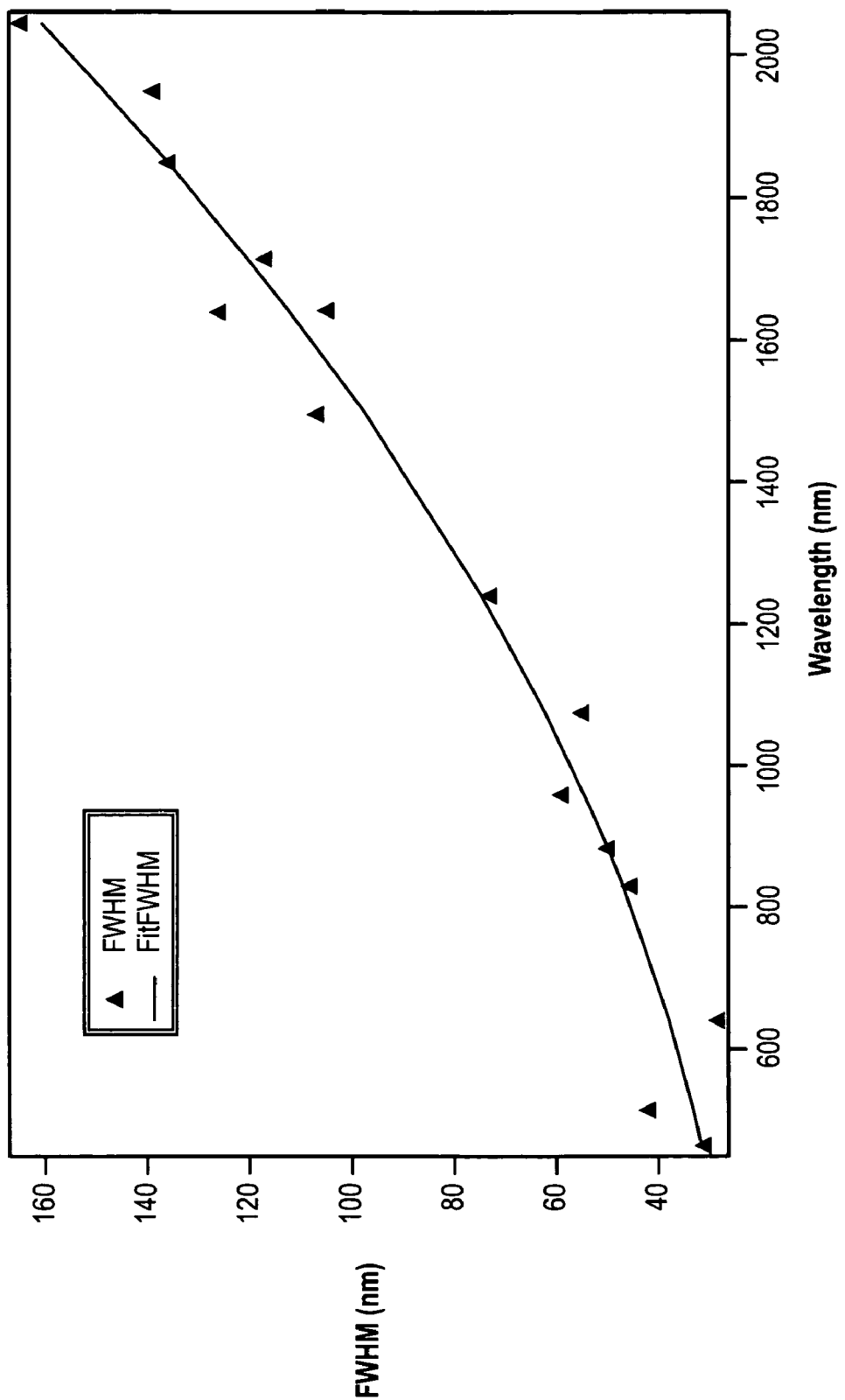
FIG. 3B is a chart illustrating the spectral width of each LED in FIG. 3A.

As a baseline for measuring the effects of temperature on LED photon wavelength and intensity, FIG. 3A illustrates the spectra of a variety of LEDs formed of III-V semiconductor compounds measured at room temperature (about 295 K). The intensity of each LED in FIG. 3A has been arbitrarily normalized. FIG. 3B is a chart illustrating the spectral width of each LED in FIG. 3A. In FIG. 3B, the spectral width of each LED is determined by computing its full-width at half-maximum value (FWHM) using the data from FIG. 3A. An LED's FWHM value is equal to the absolute difference between the wavelengths at which the spectral radiant intensity is 50 percent of the maximum power. The FWHM of each LED from FIG. 3A is represented in FIG. 3B by triangular shapes labeled "FWHM". These discrete FWHM measurements have also been fitted to equation 3 curve using the least squares curve fitting method, represented by the solid line labeled "FitFWHM". As seen in these figures, the spectral width of a LED is broadened as its wavelength increases.

Figure 4:
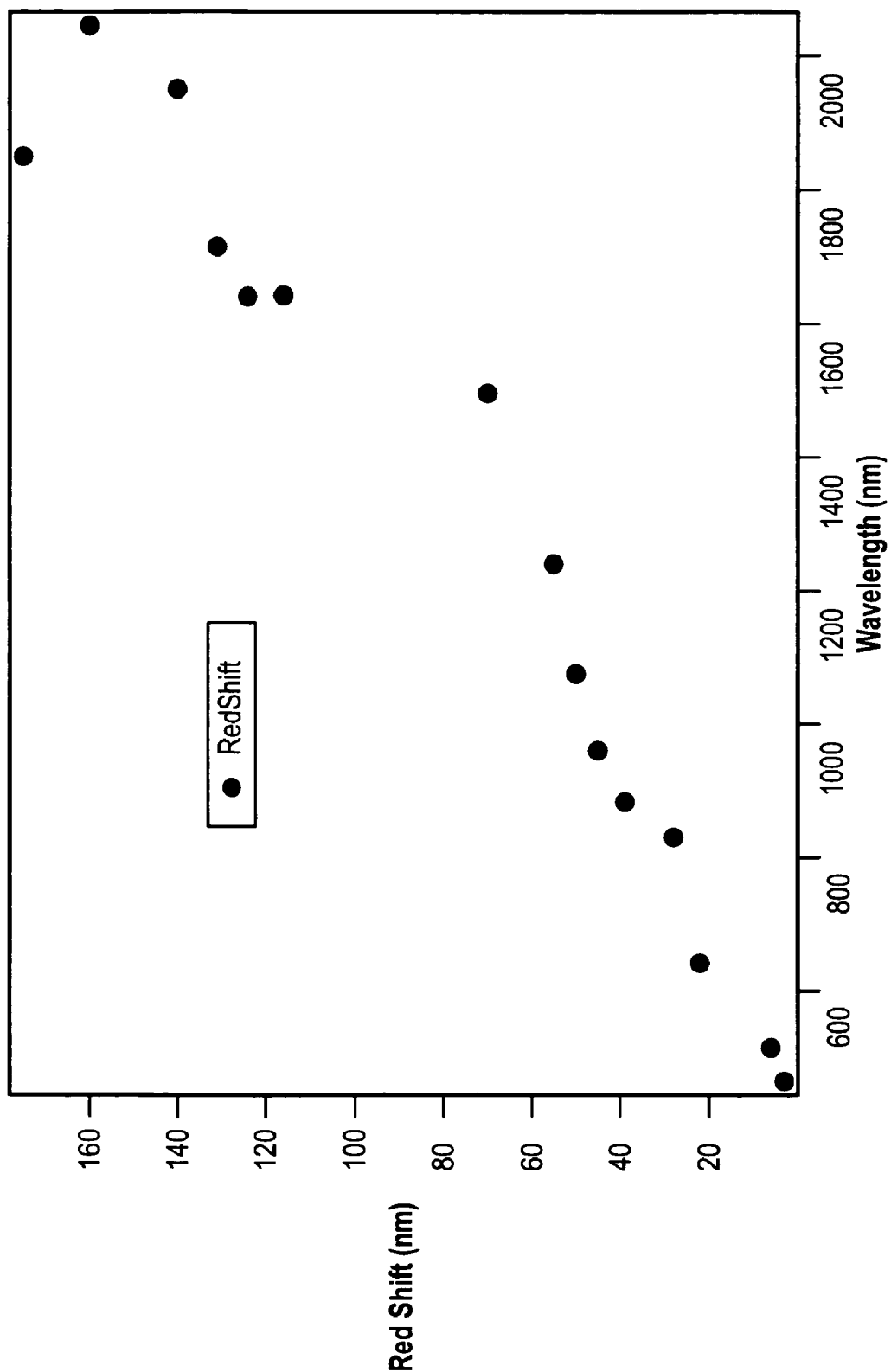
FIG. 4 is a chart illustrating the amount of red-shift (in nm) experienced by each LED in FIG. 3A during a specified temperature change.

By comparison, as the ambient temperature (and hence the p-n junction temperature of each LED) increases, the bandgap of the LED effectively shrinks, resulting in the emission of peak photons having wavelengths that are longer than those that would be emitted by the LED at room temperature. This phenomenon, commonly referred to as "red-shift", is illustrated in FIG. 4. FIG. 4 is a chart illustrating the total amount of red-shift (in nm) experienced by the peak photon wavelength of each LED in FIG. 3A during a specified temperature change (from 25° C. to 165° C., or $\Delta T = 140°$ C.). Generally speaking, the magnitude of the red-shift increases as the bandgap decreases. In other words, the larger the bandgap of the LED's semiconductor material, the less sensitive the LED will be to temperature effects.

While obtaining the measurements illustrated in FIG. 4, red-shifts were observed to range from 0.02 nm per degree Celsius at 465 nm to as much as 1.14 nm per degree Celsius at 2045 nm. Unfortunately, this range of temperature shifts is greater than the width of the vibrational bands observed in hydrocarbon mixtures (see, for example, FIG. 2). Thus, according to some embodiments, the red-shifts resulting from increased temperatures must be mitigated in order for LED 106 to serve as an appropriate light source for analyzing hydrocarbon mixtures in a downhole environment.

Figure 5:
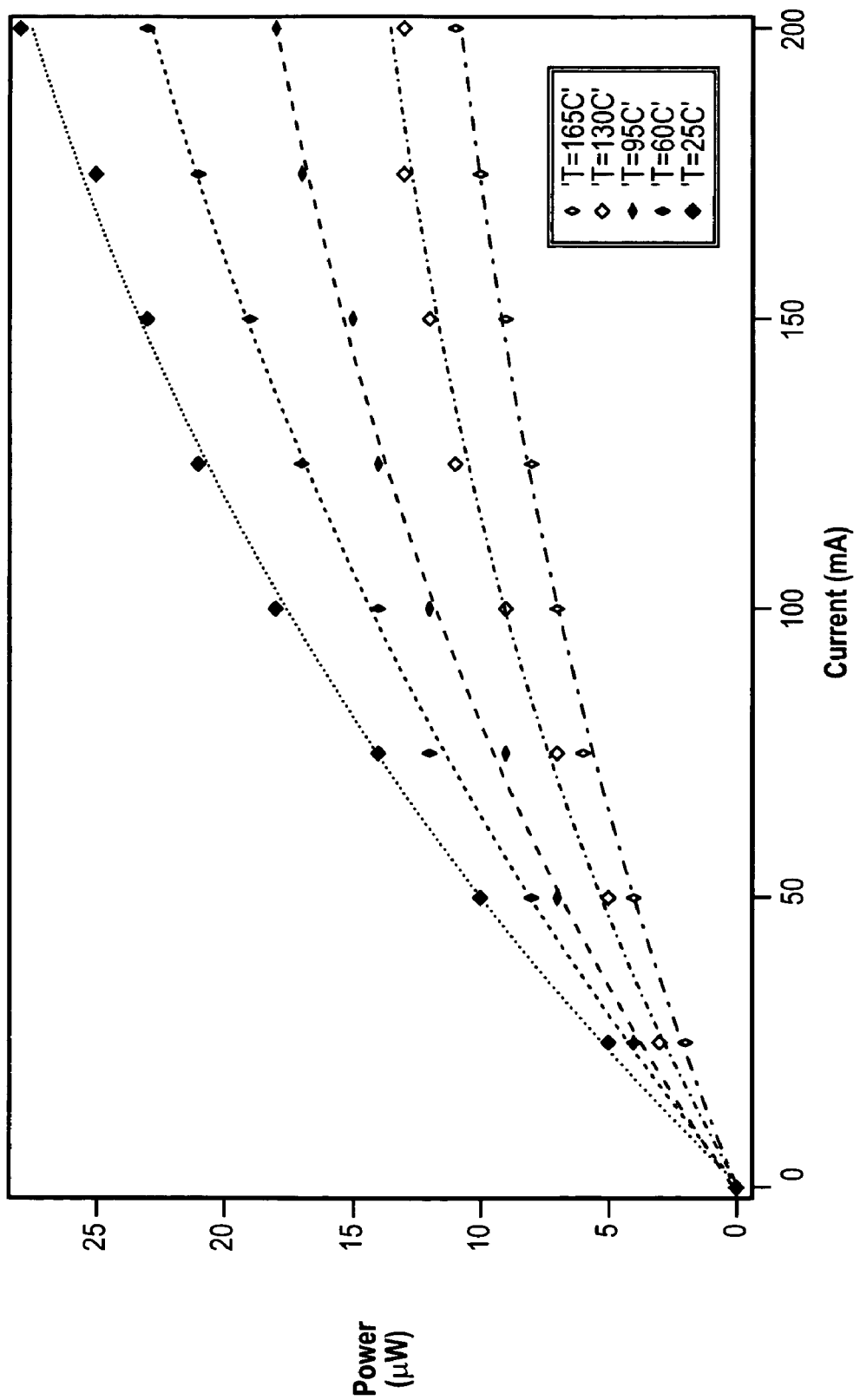
FIG. 5 is a chart illustrating the adverse effects of temperature on the power efficiency of a near-infrared LED.

Moreover, aside from causing red-shift, increased p-n junction temperature results in lower LED efficiency due to a rapid increase in the non-radiative Auger recombination rate and carrier leakage over the heterostructure barriers. FIG. 5 illustrates the adverse effects of temperature on the power output of a near-infrared LED (1496 nm). As seen in this figure, the amount of driving current required to produce the same amount of power (in microwatts) increases as temperature is increased. Thus, as with the red-shift phenomenon described above, according to some embodiments this decrease in power efficiency resulting from increased temperatures must be mitigated in order for LED 106 to serve as an appropriate light source for analyzing hydrocarbon mixtures in a downhole environment.

According to at least one embodiment, the above-described negative red-shift effects resulting from a LED's sensitivity to temperature are mitigated by using an optical filter 116 coupled to the output of each LED 106, as illustrated in FIG. 1A. When coupled together in this manner, LED 106 and optical filter 116 form a LED/filter pair 118. By filtering the output of each LED 106 using an optical filter 116, wavelength shifting is nearly eliminated in the required temperature range.

In many embodiments, optical filter 116 is an optical bandpass filter. The center frequency and bandwidth of optical filter 116 may be matched with the parameters of LED 106 to ensure that only a pre-selected wavelength band corresponding to a desired spectral characteristic is allowed to pass through the filter. For example, the center frequency and bandwidth of optical filter 116 may be matched with the parameters of LED 106 to ensure that only wavelength bands corresponding to the vibrational bands of hydrocarbon are allowed to pass through the filter, thereby enabling a user of fluid analysis cell 100 to detect the presence and amount of hydrocarbon in fluid sample 104. In at least one embodiment, optical filter 116 has a bandwidth of 15-20 nm. According to some embodiments, the optical filters 116 are matched with the parameters of LEDs 106 to provide the required OD resolution across the range of 1070 nm to 2008 nm at temperatures between 0 and at least 165° C. Other embodiments limit the range for LED 106/filter 116 combinations to wavelengths between 1445 nm and 2008 nm, or between 1600 nm and 1760 nm, or between 1600 to 2008 nm. Other embodiments such as FIG. 1B may also include the visible range for LED 206/filter combinations wavelengths between 400 nm and 750 nm. Other combinations may also be used, and especially ranges that include hydrocarbon peaks and other fluids of interest.

Figure 6A:
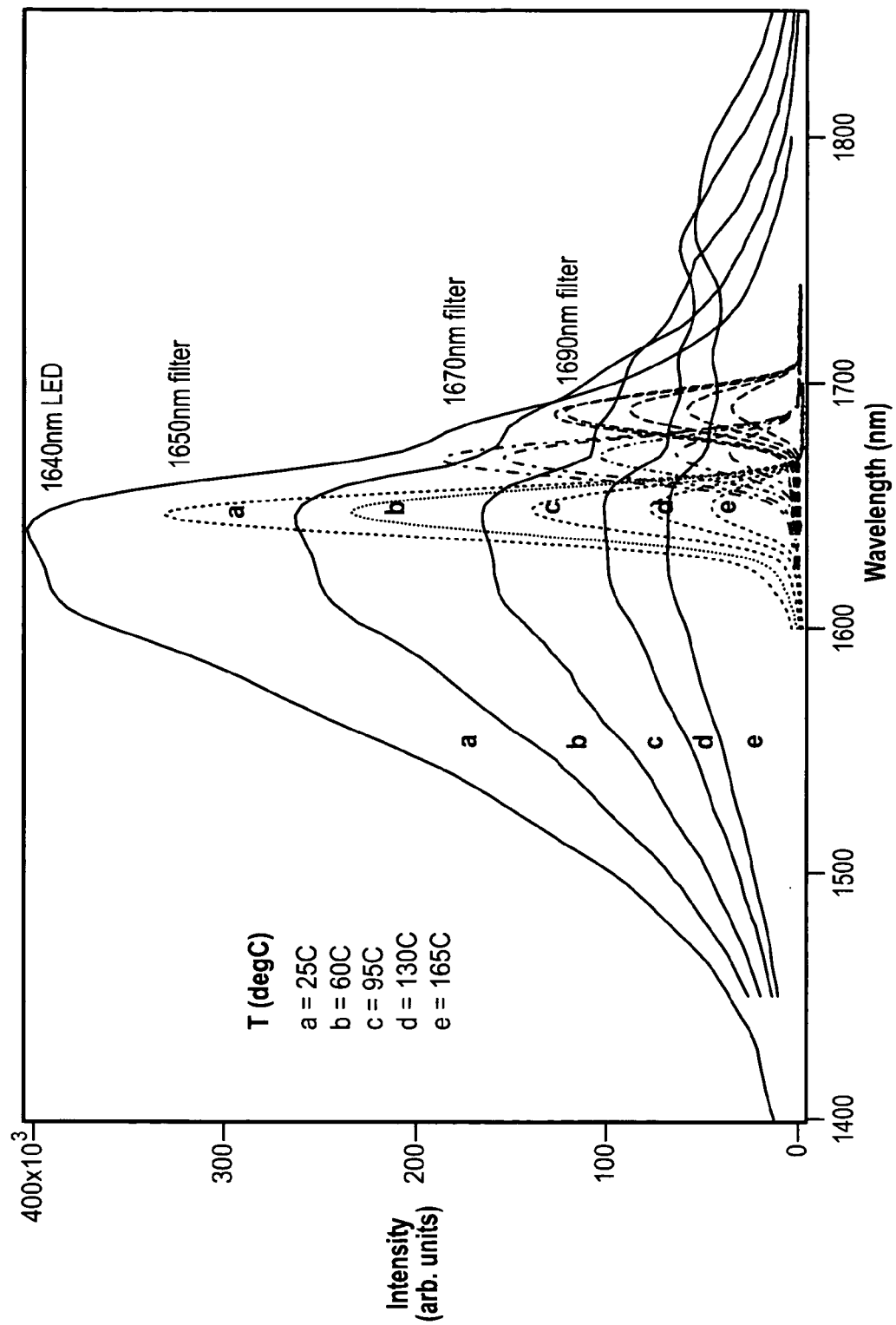
FIG. 6A is a chart illustrating the positive effects of optical filters on red-shifting.

FIG. 6A is a chart illustrating the positive effects of optical filters on red-shifting. The solid lines illustrate the spectral characteristics of a 1640 nm LED operating at a variety of ambient temperatures (a, b, c, d and e), while the dotted and dashed lines illustrate the spectral characteristics of the same LED respectively coupled to a 1650 nm filter, a 1671 nm filter, and a 1690 nm filter. As seen in this figure, the wavelength of the peak photon in the 1640 nm LED gradually increases as the ambient temperature increases from temperature "a" (25° C.) to temperature "e" (165° C.). Advantageously, by coupling an optical filter to the output of the 1640 nm LED, the red-shift effects are mitigated. For example, as illustrated in FIG. 6A, the red-shift temperature effect is shown to be greatly reduced when a 1650 nm filter is applied to the LED's output. Namely, the wavelength of the peak photon emitted by the 1640 nm LED remains approximately the same as the ambient temperature increases from temperature "a" to temperature "e." The same holds true for the 1671 nm and 1690 nm filters.

Figure 6B:
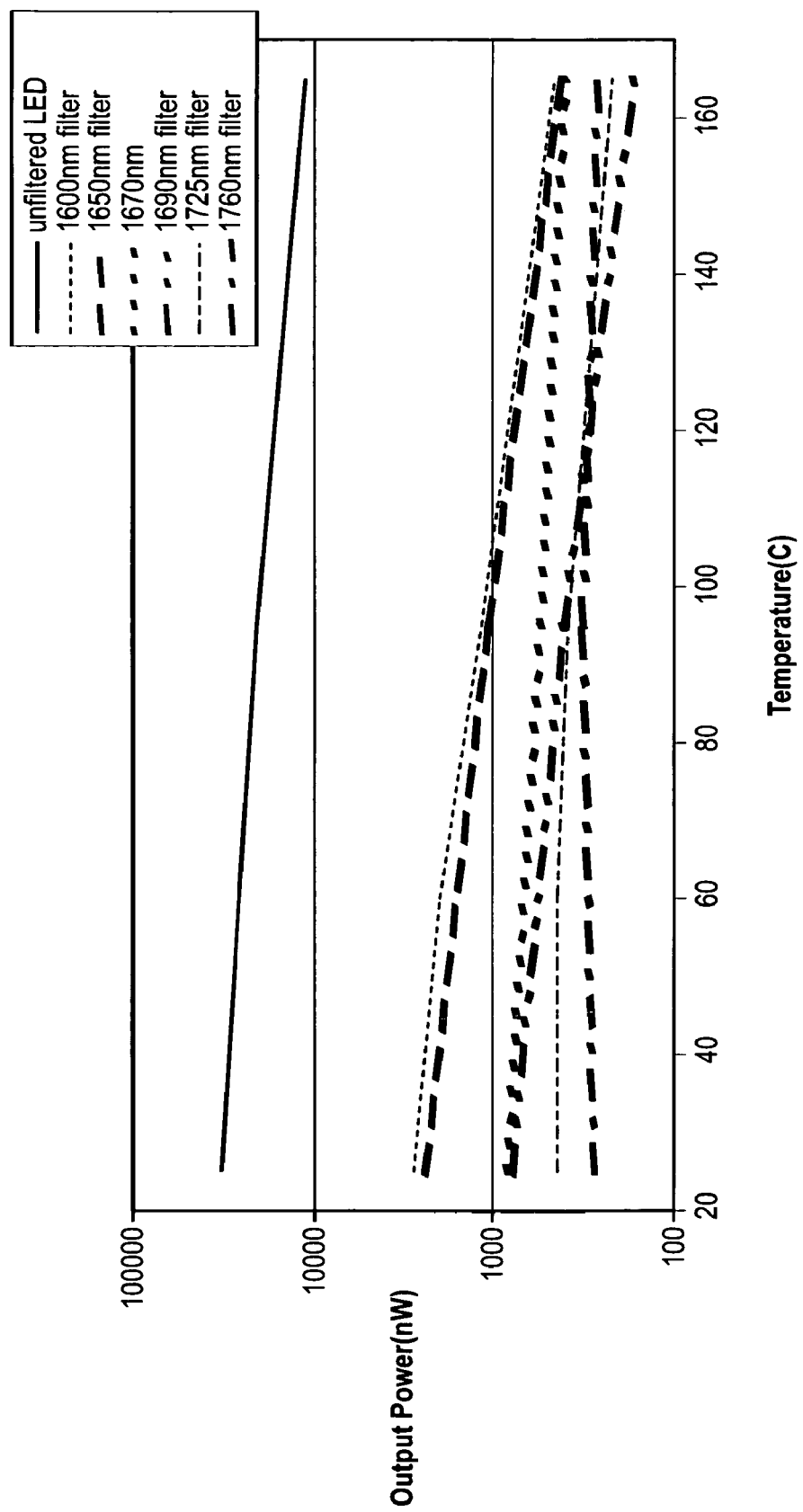
FIG. 6B is a chart illustrating the effects of optical filters on LED power efficiency.

FIG. 6B is a chart illustrating the effects of optical filters on LED power efficiency. The data in this figure was obtained by measuring the power output of an unfiltered 1640 nm LED driven by a constant current of 200 mA while the ambient temperature was increased from 25° C. to 165° C. The power output of the same 1640 nm LED driven using the same current was then measured after being filtered by filters of various wavelengths (1650 nm, 1671 nm, 1690 nm, 1725 nm, and 1760 nm, respectively). The majority of the filters exhibited power-efficiency losses much larger than the losses of the unfiltered LED, because the emission intensity within the fixed spectral filter window varies due to the temperature sensitivity of the band gap. In some cases (such as the 1760 nm filter), the power may instead increase at higher temperatures. In some embodiments, the LED band gap may be chosen to maximize the coupling efficiency of the LED 106 and optical filter 116 over a certain temperature range.

Advantageously, even though the power output of each LED/filter pair illustrated in FIG. 6B is not constant over the entire range of tested temperatures, changes in intensity of LED 106 will not adversely affect the accuracy of fluid sample cell 100. This is because optical density measurements are based on the ratio of two signals; namely, $I_0$ and I, as set forth in Eq. 1. In other words, as long as the incident light signal $I_0$ is recorded in real-time, changes in the transmitted light signal I will be compensated for in Eq. 1 by changes in the incident light signal $I_0$. However, because photodetector 112 can only detect light signals of certain minimal intensities, the wavelength of LED/filter pair 118 must be carefully chosen to ensure adequate intensity at photodetector 112, particularly when the LED/filter pairs 118 are not actively cooled.

Thus, by selectively coupling the output of LED 106 with an appropriate optical filter 116 in the manner described above, red-shifting is nearly eliminated in the required temperature range. Therefore, LED 106 in fluid analysis cell 100 can be successfully adapted for use in the downhole environment according to principles of the present invention.

Although fluid analysis cell 100 has been described above as only requiring a single LED 106 for operation, one of ordinary skill in the art having the benefit of this disclosure will recognize that a plurality of LEDs 106 may be coupled to sample window 110 and/or reference photodetector 114, as illustrated in FIG. 1A. This may be done, for example, to enable the simultaneous detection of a plurality of desired wavelengths. For example, if a user is interested in detecting the presence of both methane and carbon-dioxide, LEDs 106 having wavelengths of 1671 nm and 2008 nm, respectively, might be coupled to sample window 110. Furthermore, as with the single LED/filter pair 118 described above, the output of each of a plurality of LEDs 106 may also be coupled to an optical filter 116, resulting in the formation of a plurality of LED/filter pairs 118. In addition, although not specifically illustrated in FIG. 1A, a cooling element similar to cooling elements 214 in FIG. 1B (described in greater detail below) may be thermally coupled to each LED/filter pair 118 in order to mitigate the adverse power-efficiency effects of increased temperature.

FIG. 1B is a schematic diagram of one embodiment of an exemplary fluid analysis cell. In at least one embodiment, exemplary fluid analysis cell 200 comprises a flowline 202 housing an extracted formation fluid sample 204. Exemplary fluid analysis cell 200 also comprises a plurality of LED/microfilter pairs 206 arranged in a matrix. LED/microfilter pairs 206 generally comprise a microfilter coupled to the output of an LED, such as LED 106 in FIG. 1A. Although the size and shape of the LED/microfilter matrix is variable, in at least one embodiment the LED/microfilter pairs 206 are arranged into a 3 by 3 matrix, and at least one other embodiment is arranged into a 2 by 2 matrix.

In accordance with certain embodiments, focusing optics 208 are provided between LED/microfilter pairs 206 and a sample window 210. Focusing optics 208 generally comprise any form of focusing optics known to those of skill in the art, including, for example, a convex lens. In at least one embodiment, focusing optics 208 serve to focus the photons of light 207 emitted by LED/microfilter pairs 206 into a collimated beam directed at sample window 210. As with sample windows 110, 111, sample windows 210, 211 may be formed of any generally transparent material capable of transmitting light, including, for example, sapphire, glass and so on.

Once the photons of light 207 are directed to sample window 210 by focusing optics 208, they are then transmitted through sample window 210, across fluid sample 204, and through a second sample window 211. The light 207 that passes through the second sample window 211 is then detected by a plurality of photodetectors 212 arranged in a matrix. As with photodetectors 112, photodetectors 212 may be formed generally of any suitable semiconducting material capable of detecting photon light emissions. For example, photodetectors 212 may be Indium-Gallium-Arsenide (InGaAs) photodiodes or Silicon (Si) photodiodes. In addition, although the size and shape of the photodetector matrix is variable, in accordance with at least one embodiment the number of photodetectors 212 is equal to the number of LED/microfilter pairs 206.

Although not illustrated in FIG. 1B, as with fluid analysis cell 100 in FIG. 1A, LED/microfilter pairs 206 may also be optically coupled to a reference photodetector. This reference photodetector may be formed generally of any suitable semiconducting material capable of detecting photon light emissions. For example, reference photodetector may be an Indium-Gallium-Arsenide (InGaAs) photodiode or a Silicon (Si) photodiode.

In order to increase the accuracy and efficiency of fluid analysis cell 200, each photodetector 212 in the matrix may be chosen based on how closely its response curve matches the wavelengths and intensities of light output by each respective LED/microfilter pair 206. In other words, photodetectors 212 having response curves closely matching the spectral frequencies of the energy output by their respective LED/microfilter pairs 206 may be chosen so as to increase the accuracy of fluid analysis cell 200.

In addition, in order to further mitigate the adverse effects of increased temperatures (commonly experienced in downhole environments), fluid analysis cell 200 may further comprise one or more cooling elements 214 thermally connected to the matrix of LED/microfilter pairs 206 and/or the matrix of photodetectors 212. Cooling elements 214 generally represent any number of cooling elements known to those of skill in the art, including, for example, single or multi-stage Peltier plates and heat sinks. Cooling elements 214 help increase the accuracy and efficiency of fluid analysis cell 200 in a number of ways, including, for example, by reducing or eliminating red-shift, by mitigating the above-described loss in LED power-efficiency due to increased temperatures, and by minimizing the aging of LEDs that occur as a result of operating at elevated temperatures. In addition, because the power required to discretely cool each of a plurality of LEDs and/or a plurality of photodetectors is substantially higher than that required to simultaneously cool a matrix of LED/microfilter pairs 206 and/or a matrix of photodetectors 212, substantial power efficiencies may be advantageously attained.

By mounting LED/microfilter pairs 206 directly onto fluid analysis cell 200, the coupling losses associated with conventional fiber optic assemblies can be avoided, resulting in the conservation of optical power. Moreover, by eliminating the need for such conventional fiber optic assemblies, the size of fluid analysis cell 200 may be reduced, resulting in a smaller sensor footprint. The compact matrices of LED/microfilter pairs 206 and photodetectors 212 additionally result in further decreases in the overall size of fluid analysis cell 200. In addition, by selecting photodetectors 212 having response curves closely matching the characteristics of each LED/microfilter pair 206, the overall efficiency and accuracy of fluid analysis cell 200 is increased.

Figure 7:
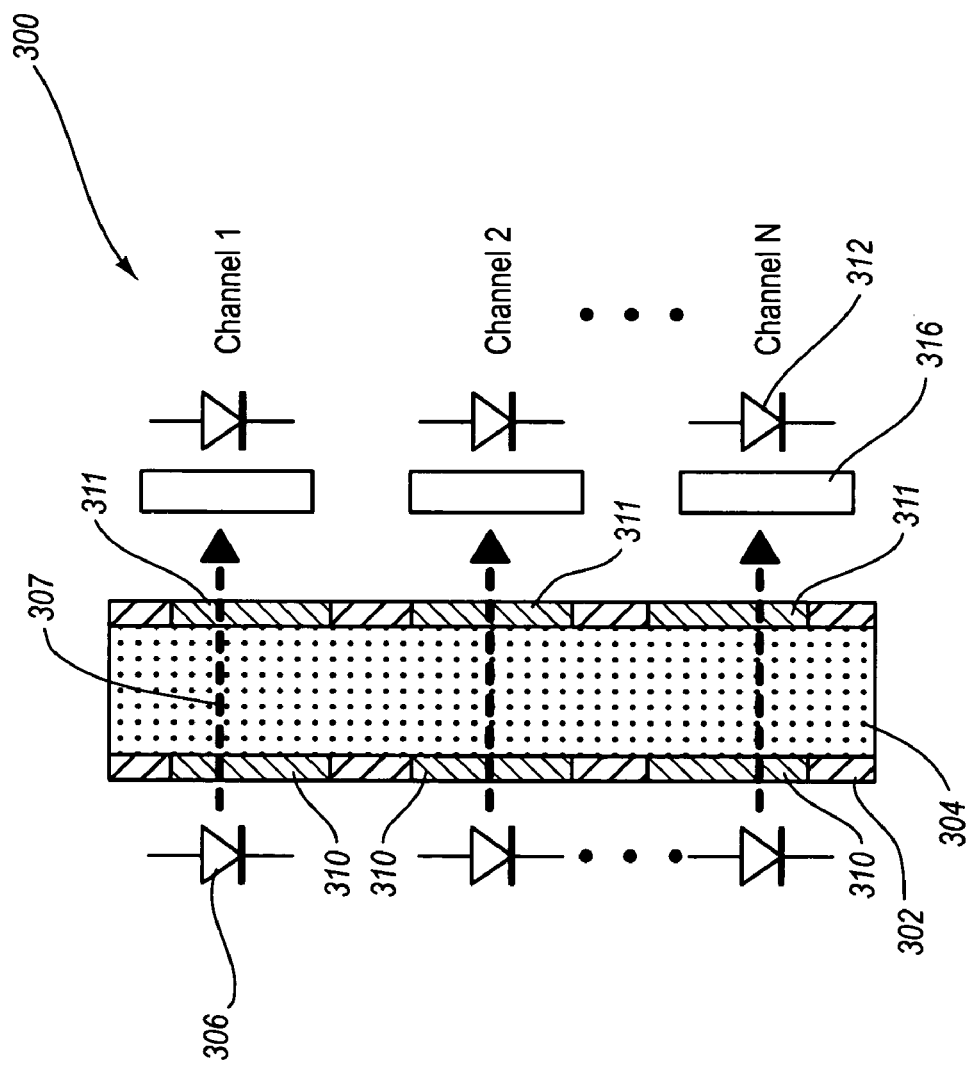
FIG. 7 is a schematic diagram of another embodiment of an exemplary fluid analysis cell according to principles of the present invention.

FIG. 7 is a schematic diagram of another embodiment of an exemplary fluid analysis cell according to principles of the present invention. According to at least one embodiment, exemplary fluid analysis cell 300 comprises a flowline 302 housing an extracted formation fluid sample 304. Exemplary fluid analysis cell 300 also comprises a plurality of LEDs 306 arranged in parallel along flowline 302. Although not illustrated, in certain embodiments LEDs 306 may be optically coupled via optical cabling to their respective sample windows 310 formed in flowline 302. In addition, although not illustrated, LEDs 306 may also be optically coupled via optical cabling to a reference photodetector.

In at least one embodiment, the photons of light 307 emitted by each respective LED 306 are directed by optical cabling onto and through their respective sample windows 310, across fluid sample 304, and through their respective second sample windows 311. The light 307 transmitted through the second sample windows 311 is then filtered by optical filters 316 and detected by photodetectors 312.

By arranging a plurality of LEDs 306 in parallel along flowline 302, various differing measurements of fluid sample 304 may be taken simultaneously. For example, the parameters of each LED 306 may be varied such that the presence or absence of a number of differing chemical compositions may be ascertained simultaneously. Alternatively, the parameters of each LED 306 may equal one another for redundancy purposes to account and/or compensate for variations in component accuracy. Accordingly, the arrangement of fluid analysis cell 300 in FIG. 7 may advantageously result in various increases in efficiency and accuracy.

Figure 8:
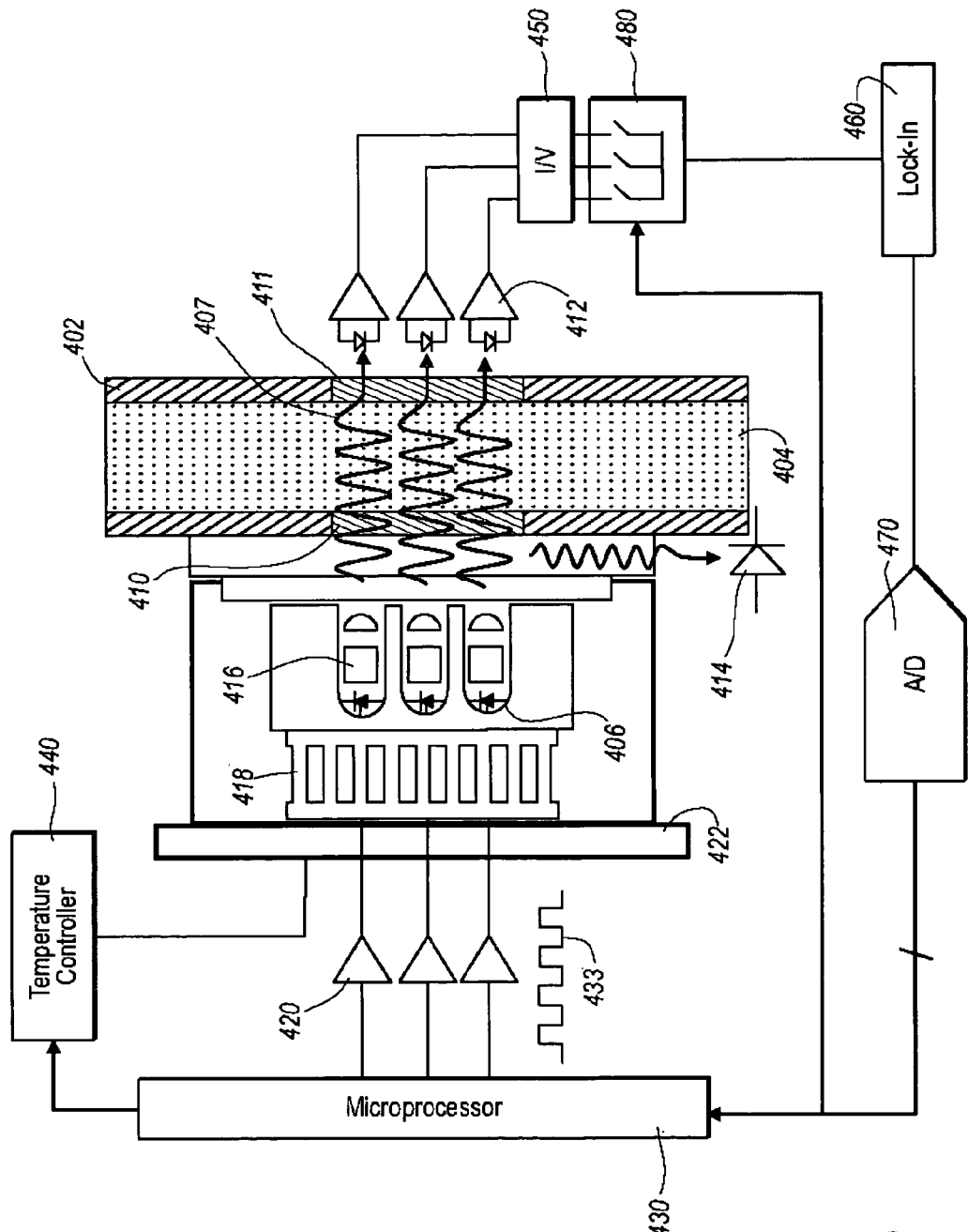
FIG. 8 is a schematic diagram of various electronic components adapted for use in connection with an exemplary fluid analysis cell according to principles of the present invention.

FIG. 8 is a schematic diagram of various electronic components adapted for use in connection with an exemplary fluid analysis cell. According to at least one embodiment, LED driver 420 forward biases LEDs 406, resulting in the spontaneous emission of photons of light 407 by the LEDs. LED driver 420 generally represents any of various adjustable or constant-current drivers known to those of skill in the art, including, for example, packaged integrated circuits and/or discrete transistor/resistor/capacitor combinations.

Microprocessor 430 generally represents any form of computing or controlling device capable of performing any number of logic and/or controlling operations. In many embodiments, microprocessor 430 addresses and controls the operation of each LED driver 420. Microprocessor 430 may also generate a digital pulse signal 433 for digitally modulating LEDs 406. The digital pulse signal 433 comprises an encoding sequence known to those of skill in the art having the benefit of this disclosure, and may include, for example, a Hadamard or M-Sequence. In another embodiment, the pulses may comprise a series of sign waves of different frequencies.

The temperature and operation of a cooling element 418 in housing 422 may be controlled by temperature controller 440, which may in turn be controlled by microprocessor 430. Microprocessor 430 may be formed of any number of discrete or integrated circuits, including, for example, a multiplexer/de-multiplexer 480 for separating/combining the various switching signals sent to or from LEDs 406, and/or a signal generator for generating digital pulse signal 433.

After passing through optical filters 416, light 407 emitted by LEDs 406 is transmitted through sample window 410, across a fluid sample 404 housed in flowline 402, and through another sample window 411 where it is detected by photodetector 412. Although not specifically illustrated in FIG. 1B, optical filters may also be placed both on LED sources 206 and on photodiode detectors 212, in order to enable simultaneous operation of all LEDs 206 without pulse encoding.

Transimpedance amplifier 450, the input of which is connected to the output of photodetector 412, then converts the current detected by photodetector 412 into voltage. Transimpedance amplifier 450 generally represents any form of electrical or mechanical device capable of converting current into voltage. As illustrated in FIG. 8, in certain embodiments more than one detector may be employed and each photodiode output is connected to a corresponding transimpedance amplifier input.

In certain embodiments, the output of transimpedance amplifier 450 is connected to the input of multiplexer 480, which is controlled by microprocessor 430. The output of multiplexer 480 is connected to the input of an A/D converter 470. Microprocessor 430 analyzes the correlation of the input signals. The input signals may be of a pulsed variety or continuous depending on the particular embodiment.

In certain embodiments, the output of transimpedance amplifier 450 or multiplexer 480 is connected to the input of a lock-in amplifier 460. Lock-in 460 represents any form of lock-in amplifier known in the art, including, for example, pre-packaged integrated circuit lock-in amplifiers and digital-signal-processing (DSP) lock-in amplifiers. As will be known to those of skill in the art, lock-in amplifier 460 serves to "lock-in" on the relatively small optical signal detected by photodetector 412 by focusing on a particular frequency of interest. Lock-in amplifier 460 helps to increase the overall accuracy and efficiency of fluid analysis cell 400.

According to at least one embodiment, the output of lock-in amplifier 460 is connected to the input of an analog-to-digital (A/D) converter 470, which may be formed of any circuit or device capable of converting an analog signal to a digital one. A/D converter 470 converts the analog signal transmitted from lock-in amplifier 460 into a digital signal and supplies the converted signal to microprocessor 430. Although the digital signal transmitted by A/D converter 470 to microprocessor 430 may contain any number of data values, in many embodiments this signal contains data detailing the intensity of the transmitted light I detected by photodetector 412.

Although not specifically illustrated in FIG. 8, similarly to photodetector 412, the output of reference photodetector 414 may be connected to one or more of a transimpedance amplifier, a lock-in amplifier, and/or an A/D converter. As with photodetector 412, a transimpedance amplifier may convert the signal detected by reference photodetector 414 into voltage, a lock-in amplifier may "lock-in" on a specific frequency to increase accuracy, and/or an A/D converter may convert the analog signal into a digital one. The resulting signal, which in many embodiments digitally represents the intensity of incident light $I_0$ detected by reference photodetector 414, may then be supplied to microprocessor 430 for use in computing the optical density of fluid sample 404. Thus, in accordance with Eq. 1 and based on the signals supplied by reference photodetector 414 and photodetector 412, microprocessor 430 computes the presence and/or amount of any of a number of chemical compositions in fluid sample 104.

Accordingly, by providing a microprocessor 430 having a signal generator 433 for digitally modulating LEDs 406, the need for a mechanical chopper wheel and motor is obviated, thereby avoiding the potential mechanical failures inherent in conventional downhole spectrometers. In addition, because LEDs are more compact and are more resistant to shock and vibration than conventional incandescent lamps, additional advantages in size and ruggedness are attained over conventional spectrometers. Moreover, because LEDs use a fraction of the energy required to power conventional incandescent lamps, additional increases in power-efficiency are attained.

Although the foregoing descriptions of FIG. 8 have been provided with reference to discrete elements and circuits, one of skill in the art having the benefit of this disclosure will recognize that one or more of these discrete circuits may be combined into a single integrated circuit or chip. For example, while transimpedance amplifier 450 and lock-in amplifier 460 have been illustrated as discrete elements, the function of these two circuits may be combined into a single integrated circuit, resulting in increased savings in space and efficiency. One of skill in the art having the benefit of this disclosure will also recognize that one or more of the elements in FIG. 8 may be software-implemented, as opposed to being hardware-implemented.

The preceding description has been presented only to illustrate and describe the invention and some examples of its implementation. This exemplary description is not intended to be exhaustive or to limit the invention to any precise form disclosed. Many modifications and variations are possible in light of the above teaching. For example, one of ordinary skill in the art will appreciate that the principles, methods and apparatus disclosed herein are applicable to many oilfield operations, including MWD, LWD, PL and wireline operations.

The preceding description is also intended to enable others skilled in the art to best utilize the invention in various embodiments and aspects and with various modifications as are suited to the particular use contemplated. It is intended that the scope of the invention be defined by the following claims.

What is claimed is:

1. An apparatus for analyzing a hydrocarbon mixture, comprising:
    at least one light-emitting diode (LED);
    at least one photodetector positioned to detect energy transmitted by said LED through a sample of said hydrocarbon mixture or back scattered from said hydrocarbon mixture; and
    at least one optical bandpass filter for filtering the energy transmitted by said LED.

2. The apparatus according to claim 1 wherein parameters of said optical bandpass filter are chosen to mitigate a temperature dependent wavelength shift of said LED.

3. The apparatus according to claim 1 wherein parameters of said optical bandpass filter are selected to allow passage of a pre-selected wavelength band.

4. The apparatus according to claim 3 wherein said pre-selected wavelength band corresponds to at least one spectral characteristic of hydrocarbon.

5. The apparatus according to claim 4 wherein the bandwidth of said optical bandpass filter is between 15-20 nm.

6. The apparatus according to claim 1 wherein parameters of said LED and said optical bandpass filter are selected to enable analysis of live hydrocarbon mixtures in a downhole environment.

7. The apparatus according to claim 1 wherein
    said at least one LED comprises a plurality of LEDs arranged in a matrix; and aid at least one photodetector comprises a plurality of photodetectors arranged in a matrix and respectively positioned to detect energy transmitted by said plurality of LEDs through said sample.

8. The apparatus according to claim 7 wherein said at least one optical bandpass filter comprises a plurality of optical bandpass filters for respectively filtering the energy transmitted by said plurality of LEDs.

9. The apparatus according to claim 8 wherein a response curve of each of said plurality of photodetectors is respectively matched to parameters of said plurality of optical bandpass filters.

10. The apparatus according to claim 7 further comprising a processor for controlling the operation of said plurality of LEDs, for digitally modulating said plurality of LEDs, and for analyzing said sample.

11. The apparatus according to claim 10 further comprising:
    a transimpedance amplifier, an input of which is connected to an output of said plurality of photodetectors;
    a lock-in amplifier, an input of which is connected to an output of said transimpedance amplifier; and an analog-to-digital converter, an input of which is connected to an output of said lock-in amplifier and an output of which is connected to said processor.

12. The apparatus according to claim to claim 7, further comprising a cooling element in thermal communication with said plurality of LEDs.

13. The apparatus according to claim 7, further comprising focusing optics positioned between said plurality of optical bandpass filters and said sample for focusing the energy transmitted by said plurality of LEDs.

14. The apparatus according to claim 13 wherein said focusing optics focus the energy transmitted by said plurality of LEDs into a collimated beam.

15. The apparatus according to claim to 1, further comprising a downhole fluid sampling tool having the at least one LED and photodetector.

16. A system comprising:
a downhole live hydrocarbon mixture and a subterranean sample analysis tool, the subterranean sample analysis tool comprising:
a plurality of light-emitting diodes (LEDs) arranged in a matrix; and
a plurality of photodetectors arranged in a matrix and respectively positioned to detect energy transmitted by said plurality of LEDs through said live hydrocarbon mixture.

17. The system according to claim 16, further comprising a cooling element in thermal communication with said plurality of LEDs.

18. An apparatus comprising:
a subterranean sample analysis tool, comprising:
a plurality of light-emitting diodes (LEDs) arranged in a matrix;
a plurality of photodetectors arranged in a matrix and respectively positioned to detect energy transmitted by said plurality of LEDs through a live hydrocarbon mixture; and
a plurality of optical bandpass filters for respectively filtering the energy transmitted by said plurality of LEDs.

19. A method for analyzing a hydrocarbon mixture, comprising:
transmitting energy through a sample of said hydrocarbon mixture using at least one light-emitting diode (LED);
detecting the energy transmitted through said sample using at least one photodetector; and
filtering the energy transmitted by said LED using at least one optical bandpass filter.

20. The method according to claim 19, further comprising selecting parameters of said optical bandpass filter to mitigate a temperature dependent wavelength shift of said LED.

21. The method according to claim 19, wherein parameters of said optical bandpass filter are selected to allow passage of a pre-selected wavelength band corresponding to at least one spectral characteristic of hydrocarbon.

22. The method according to claim 19, further comprising selecting parameters of said LED and said optical bandpass filter to enable analysis of live hydrocarbon mixtures in a downhole environment.

23. The method according to claim 19 wherein
said at least one LED comprises a plurality of LEDs arranged in a matrix; and
said at least one photodetector comprises a plurality of photodetectors arranged in a matrix and respectively positioned to detect energy transmitted by said plurality of LEDs through said sample.

24. The method according to claim 23, further comprising respectively filtering the energy transmitted by said plurality of LEDs using a plurality of optical bandpass filters.

25. The method according to claim 24, further comprising respectively matching a response curve of each of said plurality of photodetectors to parameters of said plurality of optical bandpass filters.

26. A method for analyzing a hydrocarbon mixture, comprising:
transmitting energy through a sample of said hydrocarbon mixture using a plurality of LEDs arranged in a matrix;
detecting the energy transmitted through said sample using a plurality of photodetectors arranged in a matrix and respectively positioned to detect energy transmitted by said plurality of LEDs through said sample;
controlling the operation of said plurality of LEDs using a processor;
digitally modulating said plurality of LEDs using said processor; and
analyzing spectral characteristics of said sample using said processor.

27. A method for analyzing a hydrocarbon mixture, comprising:
transmitting energy through a sample of said hydrocarbon mixture using a plurality of LEDs arranged in a matrix;
detecting the energy transmitted through said sample using a plurality of photodetectors arranged in a matrix and respectively positioned to detect energy transmitted by said plurality of LEDs through said sample;
focusing the energy transmitted by said plurality of LEDs into said sample using focusing optics.

28. An apparatus for analyzing a hydrocarbon mixture, comprising:
at least one light-emitting diode (LED);
a cooling element in thermal communication with said at least one LED, and
at least one photodetector positioned to detect energy transmitted by said LED through a sample of said hydrocarbon mixture or back scattered from said hydrocarbon mixture.

29. An apparatus for analyzing a hydrocarbon mixture, comprising:
a plurality of light-emitting diodes (LEDs) arranged in a matrix;
a plurality of photodetectors arranged in a matrix and respectively positioned to detect energy transmitted by said plurality of LEDs through a sample of said hydrocarbon mixture;
a processor for controlling the operation of said plurality of LEDs, for digitally modulating said plurality of LEDs, and for analyzing said sample;
a transimpedance amplifier, an input of which is connected to an output of said plurality of photodetectors;
a lock-in amplifier, an input of which is connected to an output of said transimpedance amplifier; and
an analog-to-digital converter, an input of which is connected to an output of said lock-in amplifier and an output of which is connected to said processor.

30. A method, comprising:
analyzing a live hydrocarbon mixture downhole, comprising:
drawing the live hydrocarbon mixture into a downhole sampling tool, and while downhole:
transmitting energy through a sample of said live hydrocarbon mixture using at least one light-emitting diode (LED); and
detecting the energy transmitted through said sample using at least one photodetector.

31. The method according to claim 30, further comprising inserting the downhole sampling tool into a borehole.

32. A method, comprising: determining chemical composition of a fluid sample downhole using a downhole LED.

33. The method of claim 32 wherein the using a downhole LED comprises:
transmitting LED energy to the sample downhole;
detecting the LED energy transmitted from the sample downhole; communicating detected LED energy measurements uphole to surface electronics;
identifying spectral absorption peaks corresponding to chemical components of the fluid sample.

34. The method of claim 32, further comprising filtering energy transmitted by said LED using a plurality of optical bandpass filters.

* * * * *